United States Patent
Harrod et al.

(10) Patent No.: US 9,475,697 B2
(45) Date of Patent: Oct. 25, 2016

(54) REMOVAL OF BROMINE FROM GASEOUS HYDROGEN BROMIDE

(71) Applicant: Albemarle Corporation, Baton Rouge, LA (US)

(72) Inventors: William B. Harrod, Minden, LA (US); John M. Harden, Zachary, LA (US); Rhett P. Heeb, Magnolia, AR (US); Steven G. Karseboom, Baton Rouge, LA (US); Gary L. Sharp, Magnolia, AR (US); Robert E. Williams, Boles, AR (US)

(73) Assignee: Albemarle Corporation, Baton Rouge, LA (US)

( * ) Notice: Subject to any disclaimer, the term of this patent is extended or adjusted under 35 U.S.C. 154(b) by 69 days.

(21) Appl. No.: 14/405,201

(22) PCT Filed: May 24, 2013

(86) PCT No.: PCT/US2013/042677
§ 371 (c)(1),
(2) Date: Dec. 3, 2014

(87) PCT Pub. No.: WO2013/184415
PCT Pub. Date: Dec. 12, 2013

(65) Prior Publication Data
US 2015/0147265 A1  May 28, 2015

Related U.S. Application Data

(60) Provisional application No. 61/655,784, filed on Jun. 5, 2012.

(51) Int. Cl.
*C01B 7/09* (2006.01)
*C07C 17/12* (2006.01)
(Continued)

(52) U.S. Cl.
CPC .............. *C01B 7/093* (2013.01); *B01D 53/68* (2013.01); *C07C 17/12* (2013.01); *C07C 17/14* (2013.01); *Y02P 20/582* (2015.11)

(58) Field of Classification Search
CPC ....... C07C 17/12; C07C 17/14; B01D 53/68; B01D 2257/2022; C01B 7/093
See application file for complete search history.

(56) References Cited

U.S. PATENT DOCUMENTS

| | | |
|---|---|---|
| 2,520,947 A | 9/1950 | Matuszak |
| 4,287,373 A | 9/1981 | Garman et al. |
| 7,408,088 B1 | 8/2008 | McKinnie |

FOREIGN PATENT DOCUMENTS

| | | |
|---|---|---|
| CN | 102001627 A | 4/2011 |
| WO | 2010059324 A2 | 5/2010 |
| WO | 2012092338 A2 | 7/2012 |

OTHER PUBLICATIONS

"Gmelins Handbuch der Anorganische Chemie" Aug. 21, 1931; Verlag Chemie Gmbh, Weinheim/Bergstr. und Berlin, vol. Brom, pp. 185-187; 3 pages; translation, 8 pages.

(Continued)

*Primary Examiner* — Jafar Parsa
*Assistant Examiner* — Medhanit Bahta
(74) *Attorney, Agent, or Firm* — Marcy M. Hoefling

(57) ABSTRACT

Processes of and systems for removing free bromine from gaseous anhydrous HBr contaminated with free bromine are described. In one type of process the gaseous contaminated HBr is fed into countercurrent contact with at least one liquid alkylaromatic hydrocarbon within a packed section of a column while maintaining the packed section under free radical bromination conditions so that one or more than one liquid a-bromoalkylaromatic compound is produced along with one mole of gaseous HBr per mole of a-bromoalkylaromatic compound produced. In another type of process the gaseous anhydrous HBr is fed into countercurrent contact through at least two scrubbers so that the gaseous anhydrous HBr is scrubbed substantially free of bromine by passage through these at least two scrubbers, each of which contains a different specified type of scrubbing liquid. In one embodiment the liquid alkylaromatic hydrocarbon comprises 1,2-diphenylethane.

21 Claims, 1 Drawing Sheet

(51) Int. Cl.
*B01D 53/68* (2006.01)
*C07C 17/14* (2006.01)

(56) References Cited

OTHER PUBLICATIONS

Author Unknown; "Explaining the Reaction Between Methane and Bromine", website: http://www.chemguide.co.uk/mechanisms/freerad/ch4andbr2tt.html; website visited Aug. 27, 2014; 5 pages.

Author Unknown; "Free-radical Halogenation", website: http:en.wikipedia.org/wiki/Free-radical_halogenation; website visited Aug. 27, 2014; 1 page.

Author Unknown; "Selectivity in Free Radical Reactions"; website: http://www.masterorganicchemistry.com/2013/09/23/selectivity-in-free-radical-reactions/; website visited Aug. 27, 2014; 14 pages.

Thapa, Rajesh; "Regioselectivity in Free Redical Bromination of Unsymmetrical Dimethylated Pyridines"; A Thesis Submitted to the Faculty of Miami University, Oxford, Ohio; 2009; obtained at website: http://olcl.ohiolink.edu/search/z?mu3ug+b4083461 on Mar. 10, 2015; 69 pages.

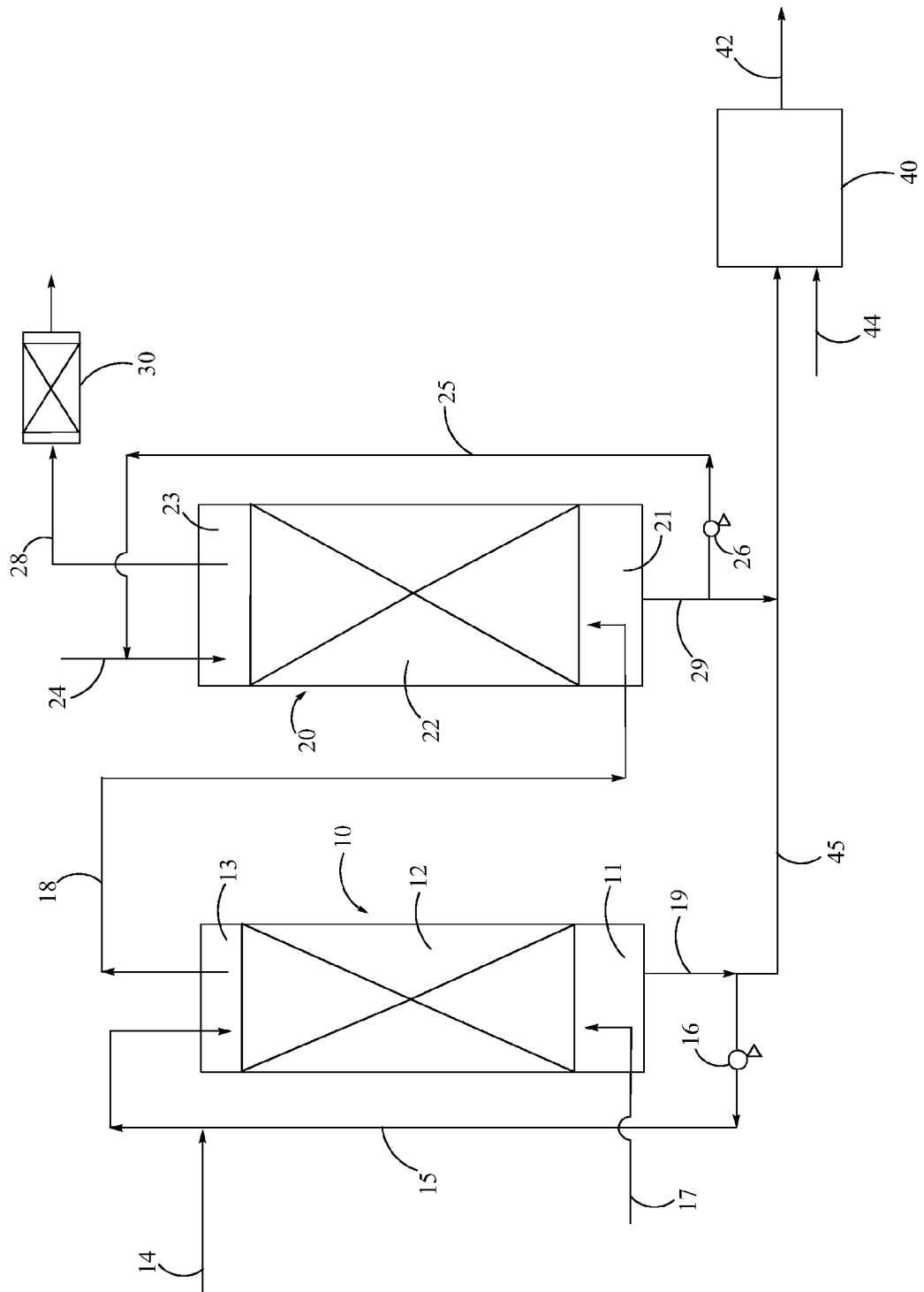

REMOVAL OF BROMINE FROM GASEOUS HYDROGEN BROMIDE

REFERENCE TO RELATED APPLICATIONS

This application is the National Stage of International Patent Appl. No. PCT/US2013/042677 filed on May 24, 2013, which in turn claims the benefit of U.S. Provisional Patent Appl. No. 61/655,784, filed on Jun. 5, 2012, the disclosures of which are incorporated herein by reference.

TECHNICAL FIELD

This invention relates to new scrubber processes and systems for purification of an anhydrous gaseous hydrogen bromide (HBr) stream containing gaseous bromine ($Br_2$). Such streams optionally may also contain trace amounts of entrained and/or vaporous organic impurities from industrial plant operations.

BACKGROUND

High purity hydrogen bromide is an important industrial raw material. Various industrial bromination processes produce gaseous by-product HBr streams or mixtures contaminated with gaseous bromine. Such streams or mixtures may also be contaminated with various organic impurities. Recovery of the HBr in highly purified form (e.g. about 98% or above and desirably about 99% or above as determined by GC) for reuse as a raw material is important both from economic and environmental standpoints. Additionally, it is of importance to remove the bromine to protect equipment such as anhydrous HBr compression systems from corrosion caused by bromine.

In commercial-scale industrial operations, it is advantageous to minimize the size of a contacting vessel for scrubbing bromine from HBr due to the demanding corrosion environment. In operations where a relatively small quantity of a gaseous mixture of HBr and bromine is available for processing, average residence time (i.e., the time the gaseous mixture and the liquid scrubber composition are in contact with each other) is of little, if any, concern. On the other hand, in plant operations where a continuous relatively large volume of gaseous mixture of HBr and bromine is available for processing, average residence times within a scrubbing vessel for removal of bromine is of considerable importance. The average residence time must be kept short in order to enable such continuously evolving relatively large volumes of the gaseous mixture to be suitably processed to remove the bromine content.

Heretofore, diphenyl oxide has been used as a scrubbing medium scrubber for removing bromine from gaseous mixtures of HBr and bromine. The resulting partially-brominated diphenyl oxide was then available for conversion to decabromodiphenyl oxide, a commercially available and versatile flame retardant used in many plastic systems. Given the stated intention of the producers of decabromodiphenyl oxide to cease production of this material, this purification route will no longer be economically attractive. In addition, the continued availability of diphenyl oxide currently appears questionable, as diphenyl oxide producers begin developing alternate outlets. Prior to this invention no equally effective and equally attractive substitute for diphenyl oxide has been known to exist. Therefore, the problem has arisen to see if it is possible to develop a new, effective, economically and environmentally attractive method for removing bromine from gaseous mixtures comprising HBr and $Br_2$, especially those in which (i) the amount of HBr predominates over the amount of $Br_2$ in the gaseous phase, (ii) where in many cases small amounts of other impurities are present in the gaseous mixture, and (iii) in operations where relatively short average residence times are to be used. It is believed that the present invention provides a solution to this problem that meets most if not all of the foregoing criteria.

BRIEF NON-LIMITING SUMMARY OF THE INVENTION

This invention provides processes and systems for achieving cost-effective separations of bromine—and also, when present, vaporized organic impurities—from gaseous anhydrous HBr mixtures. Properly designed and operated processes and systems capable of yielding high purity HBr are made available by this invention. Additionally, this invention enables economically and environmentally desirable utilization of chemical by-products in the operation of these processes and systems.

There are basically two embodiments involving scrubbing processes and systems that can be used pursuant to this invention. Although somewhat different, they both function to achieve the same result, i.e., recovery of HBr in highly purified form (e.g. about 98% or above and desirably about 99% or above as determined by GC) for reuse as a raw material and to remove the bromine to protect equipment such as anhydrous HBr compression systems from corrosion caused by bromine, while at the same time enabling utilization of chemical by-products which might otherwise require disposal.

Additionally, this invention provides an advantageous fluidity improvement for purification of anhydrous HBr contaminated with elemental bromine. This improvement can be utilized in each of the above two embodiments involving scrubbing processes and systems.

The First Basic Embodiment

Pursuant to this invention there is provided in a first such embodiment a process for purification of gaseous anhydrous HBr contaminated with elemental bromine, which process comprises feeding the bromine-contaminated gaseous anhydrous HBr into countercurrent contact with at least one liquid alkylaromatic hydrocarbon within a packed section of a column (sometimes referred to herein as "packed column" since the packing may, but need not, fill the entire column) while maintaining said packed section under free radical bromination conditions so that one or more than one liquid α-bromoalkylaromatic compound is produced along with one mole of gaseous anhydrous HBr per mole of α-bromoalkylation that takes place. As will be seen from the ensuing description, the alkyl portion of the alkylaromatic hydrocarbon can be a conventional alkyl group ($C_nH_{2n+1}$) or it can be an alkylene group ($—CH_2—)_m$. In these formulas n is a number in the range of 1 to 12, desirably in the range of 2 to 8, more desirably in the range of 2 to 4, and even more desirably n is 2, and m is in the range of 1 to 6, desirably in the range of 2 to 4, and more desirably m is 2. Typically the reaction occurs within a heated column such that the reaction zone temperature is less than about 80° C. and the average contact time within the column is less than about 12 seconds. However, in some embodiments of the invention the reaction zone temperature can be in the range of about 40 to about 105° C., or in the range of about 90 to about 101° C. In conducting this process it is desirable to separately recover (i) gaseous HBr from which at least 98% of the free bromine has been removed and (ii) the one or more than one liquid α-bromoalkylaromatic hydrocarbon. This separation makes it possible to feed at least a portion of the recovered gaseous HBr of (i) into contact with one or more subsequent liquid phases at least one of which contains an aromatic ether and a Lewis Acid bromination catalyst to remove small amounts of residual bromine that may be present therein. Such contact is typically conducted within a heated column such that the reaction zone temperature is greater than about 80° C., e.g., in the range of about 80 to about 101° C. and the reaction time within the column is less than about 12 seconds.

The processes and systems of the first basic embodiment use only one type of liquid scrubbing medium for removing the bromine from the gaseous anhydrous HBr, this type being referred to hereinafter for convenience as the "brominatable alkylaromatic scrubber" or "brominatable alkylene-bridged aromatic scrubber". Collectively, these two types of this liquid scrubbing medium can be identified as "brominatable alkyl(ene) aromatic scrubber" where the (ene) portion is present only when an alkylene group is present as a bridging group between two aromatic groups. Otherwise, the scrubber is an alkyl aromatic scrubber in which there is no bridging group. An especially preferred brominatable alkylene aromatic scrubber includes but is not limited to 1,2-diphenylethane (DPE) and oligomer forms thereof, such as 1,4'-bis(phenethyl)benzene and 1,4'-bis(phenethyl)bibenzyl, which mixture can include up to about 30 wt % of DPE.

The brominatable alkylaromatic scrubber is (i) an alkylaromatic hydrocarbon (or mixture thereof) having one or two hydrogen atoms on the α-carbon atoms of the alkyl substituents present for free radical bromination in the column packing or (ii) an α-bromoalkylaromatic hydrocarbon (or mixture thereof) having one hydrogen atom and one bromine atom of the alkyl substituents present for free radical bromination in the column packing, or (iii) a mixture of (i) and (ii). Some α-,β-dibromoalkylaromatic hydrocarbon(s) may also be present. The scrubbing medium of (i) is composed of unbrominated alkylaromatic hydrocarbon(s) which exists if used at the start of the scrubbing operation. As bromination proceeds, the scrubber becomes progressively enriched in the α-bromoalkylaromatic hydrocarbon(s) of (ii). Thus it is desirable to maintain a quantity of the unbrominated alkylaromatic hydrocarbon(s) of one in the mixture of (iii) to facilitate bromination. Nevertheless, the scrubber of (ii) can be used as the starting material, but this will require more frequent addition of the scrubber liquid to the scrubbing units. The brominatable alkylene-bridged aromatic scrubber is (iv) an oligomer comprised of two or more aromatic rings, each aromatic group (e.g., $C_6H_4$) of which is singly bonded to an alkylene (—$CH_2$—)n group in which n is a number in the range of 1 to about 4, desirably in the range of 2 to about 4, and more desirably is 2, such alkylene group thus forming a bridge between 2 successive aromatic groups: Ar(—$CH_2$—)$_n$Ar[(—$CH_2$—)$_n$Ar]$_p$ where n is as defined in this paragraph and p is 0 to about 6 provided the oligomer is a flowable liquid at the temperature within the packed portion of the packed column.

There is still another kind of brominatable alkylaromatic scrubbing medium that can be used in the practice of the first basic embodiment of this invention. This kind of brominatable alkylaromatic scrubber is a styrenic dimer, styrenic trimer, styrenic tetramer, styrenic pentamer, styrenic hexamer, or progressively higher molecular weight styrenic oligomer that is a liquid, preferably a flowable liquid, at the temperature within the packed portion of the packed column in which optionally some or all of the phenyl groups attached to the backbone may be substituted by one or more alkyl groups. This kind of brominatable alkylaromatic scrubbing medium is sometimes referred to herein, including the claims as a "styrenic brominatable alkylaromatic scrubber". The kind of brominatable alkylaromatic scrubber described in this paragraph can be in admixture with corresponding compositions in which some of the backbone has been brominated, inasmuch as when used as a scrubber, the backbone of these compositions becomes progressively enriched in bromine substituents as a result of the reaction with the free bromine impurities being scrubbed out of the HBr/$Br_2$ gaseous stream.

The styrenic kind of brominatable alkylaromatic scrubbing medium described in the immediately preceding paragraph is to be considered for the purposes of this invention a type of brominatable alkylaromatic scrubber despite the fact that (A) the α-carbon atoms are strung together by a backbone instead of being (B) α-carbon atoms of individual alkyl groups. Thus mixtures of these types (A) and (B) and/or their corresponding partially brominated derivatives can be used as scrubbers if desired.

The brominatable alkylaromatic scrubber can include only one species or a plurality of different species as long as the different individual species all are within the category of the brominatable alkylaromatic scrubber. To illustrate, the brominatable alkylaromatic scrubber can be a quantity of a single liquid alkylaromatic hydrocarbon, e.g., ethylbenzene or n-butylbenzene, etc. or (ii) a liquid mixture of different alkylaromatic hydrocarbons that are brominatable on the α-carbon atoms of at least a substantial portion of the alkyl groups, e.g., a liquid mixture of $C_1$-$C_8$ alkylbenzenes. Likewise the corresponding α-bromoalkylaromatic derivatives can be present as a part of the brominatable alkylaromatic scrubber.

The first basic embodiment of this invention discussed above is preferably conducted on a continuous or semi-continuous basis as this enables large quantities of continuously-produced bromine-contaminated gaseous anhydrous HBr to be purified on an economical basis. This embodiment preferably also includes at least one carbon bed, typically composed of activated carbon or charcoal, to remove entrained and/or vaporous organic impurities which may be present in the initial HBr and bromine gaseous mixture. Such carbon bed is typically disposed downstream from the packed column.

The Second Basic Embodiment

Preferred methods and systems of this invention utilize a multiple (i.e., at least a dual) scrubber system for bromine removal via quite selective reaction of bromine with at least two different chemical types of scrubber liquids.

Thus, this second basic embodiment of this invention provides a process of removing bromine from a gaseous mixture comprising hydrogen bromide and bromine, which process comprises passing said gaseous mixture into contact with a primary scrubber composition that removes a substantial amount (i.e., greater than 80%) of the bromine, and typically about 80.0-99.5% of the bromine, from said gaseous mixture, and passing the resultant partially debrominated gaseous mixture into contact with a secondary scrubber composition that removes additional bromine from the gaseous HBr such that the resultant purified gaseous HBr has, as determined by GC, a purity of about 98% or above and preferably about 99% or above;

A) wherein said primary scrubber composition comprises:
 (1) a mixture of alkylated aromatic hydrocarbons that includes, but is not limited to, 1,2-diphenylethane (DPE) and oligomeric forms thereof, such as 1,4'-bis (phenethyl)benzene and 1,4'-bis(phenethyl)bibenzyl, which mixture can include up to about 30 wt % of DPE, or (2) a brominatable partially brominated mixture of (1), and (3) a mixture of (1) and (2);

B) wherein said secondary scrubber composition comprises
  (4) an aluminum chloride and/or aluminum bromide bromination catalyst,
  (5) one or more activated aromatic compounds that
    (i) are thermally stable at 70° C. under nitrogen, and
    (ii) are chemically and thermally stable in the presence of HBr at least up to 120° C., (such as for example 1,2-diphenylethane, 1,4-diphenoxybenzene, bisphenol-A and diphenyl ether or mixtures of any two or more of these materials),
  (6) a partially brominated derivative of any one or more of the components of (6); and C) wherein said primary and secondary scrubber compositions are kept at temperature(s) that during the scrubbing operation maintain these respective scrubber compositions in flowable liquid states.

It is preferred to conduct the operation of the primary scrubber without use of any added bromination catalyst. Conducting the operation of the primary scrubber in the absence of an added catalyst is advantageous in that the cost, maintenance, and the delivery of a catalyst into the primary scrubber reaction zone are avoided and depending upon the amount of catalyst used in the secondary scrubbing composition (and any additional scrubbing compositions, if used), a catalyst quenching operation may become unnecessary or at least simplified.

Although diphenyl oxide and its partially brominated derivatives have previously been used as the scrubbing liquid for removing bromine from HBr, such materials undergo better utilization when employed as a secondary scrubber in accordance with the process of this invention. Thus, in the practice of this invention it is possible to use diphenyl ether as the secondary scrubber as long as diphenyl ether remains available in sufficient quantities for such use. Because of its forecasted progressively ever more limited availability it may become necessary or desirable to blend small amounts of remaining diphenyl ether with other secondary scrubber compositions referred to herein for as long diphenyl ether is economically attractive for use.

It is reported in U.S. Pat. No. 7,408,088 that gaseous mixtures of HBr and Br$_2$ have been fed to diphenyl oxide to form partially brominated diphenyl oxide, and that this reaction proceeds readily in the absence of a catalyst when using less than 2 moles of bromine per mole of diphenyl oxide. Despite these findings, more recent test work on the present invention in a test facility simulating commercial operation with short average residence or contact time (about 2 seconds) has shown that the use as the secondary scrubber composition of a crude diphenyl oxide by itself (i.e., in the absence of a catalyst), resulted in the presence of excessive quantities of unreacted bromine in the reaction mixture undergoing recirculation in a scrubbing apparatus equipped with a packed column. Therefore the use of a catalyst, especially aluminum chloride and/or aluminum bromide, in the secondary scrubber composition is deemed necessary.

Another feature of this second basic embodiment of this invention involves using a continuous or a periodic flow of fresh scrubber compositions into the respective vessels containing the first and second scrubber compositions during at least most of the time the bromine removal operations of the invention are being conducted.

In a preferred way of conducting this second basic embodiment of this invention involves contacting the respective scrubber compositions and the incoming flows of gaseous mixtures of HBr and bromine as countercurrent flows. In particular, in the above-described process the initial gaseous mixture comprising HBr and bromine and the primary scrubber composition are contacted as countercurrent flows through a first reaction vessel (e.g., a packed column), and the resultant partially debrominated gaseous mixture coming from the first reaction vessel and the secondary scrubber are contacted as countercurrent flows through a second reaction vessel (e.g., another packed column). In this connection, although reference is made herein to use of a dual scrubbing operation involving primary and secondary scrubbing compositions, it is to be understood that additional scrubbing vessels containing additional scrubber compositions can be utilized or included in the conduct of this invention if desired without departing from the scope of this invention.

It is also preferred to include in the process and the systems of the second basic embodiment of this invention at least one vessel containing a bed of carbon, typically activated carbon or charcoal, so that the flow of the gaseous anhydrous HBr and bromine can be purged of organic impurities that may be present or suspended in such gaseous flow. Normally such bed of carbon is positioned after the second scrubbing vessel as this exposes the carbon bed to a smaller quantity of liquid than if the carbon bed is disposed farther ahead in the system.

Still another feature of this invention are the findings that (1) gas flow rates and (2) ratios of gas:liquid/recycle flow rates can play an important role in achieving high levels of bromine removal from the HBr/bromine gaseous mixtures being fed to the processes and systems of this invention. Experiments on a laboratory scale using as the liquid scrubber, alkylated aromatics which include 1,2-diphenylethane and oligomers thereof such as 1,4'-bis(phenethyl)benzene and 1,4'-bis(phenethyl)bibenzyl have shown that use of incoming bromine-contaminated gaseous anhydrous HBr flow rates in the range of about 300 to about 900 mL/min., and preferably in the range of about 300 to about 400 mL/min. enable achievement of very high levels of bromine removal as compared to operations conducted at significantly higher gas flow rates. It is believed that use of such relatively low gas flow rates is advantageous in that this enables a suitably long average residence time for the free radical bromination to occur at suitably elevated temperature. For example, a feed rate of 50 mL/min. into an 18-inch packed column yielding an average residence time of approximately 9-10 seconds at temperatures in the range of about 80 to about 101° C., resulted in achievement of a 95% removal of bromine using these materials and conditions. It is believed that these laboratory results and conditions will prove helpful in scaling up to large commercial scale operations. The gas flows refer to the incoming anhydrous carrier gas or HBr stream contaminated with bromine which is introduced by feed line 17 into column 10 of FIG. 1 and the rates refer to the measured carrier gas in mL/min prior to contacting the upward flow within packing 12 from feed line 17 in FIG. 1. The liquid recycle stream in line 15 of FIG. 1 is transferred by peristaltic pump 16 at externally calibrated liquid flow rates. The ratio of gas:liquid flow rates referred to herein is the ratio for the primary scrubber of the gaseous flow rate divided by the liquid flow rate. These ranged from gas:liquid flow rate ratios of about 8:1 to about 18:1 with the lower ratio of about 8:1 being preferred.

The above and other embodiments, features, and advantages of this invention will become still further apparent from the ensuing description, appended claims, and accompanying drawing.

BRIEF DESCRIPTION OF THE DRAWINGS

FIG. 1 is a schematic process flow diagram illustrating desirable ways of carrying out a process of this invention involving either the first basic embodiment or the second basic embodiment.

FURTHER DETAILED DESCRIPTION OF THE INVENTION

From the foregoing description it will be seen that the separation of gaseous bromine from gaseous anhydrous HBr pursuant to this invention involves selective bromination of one type of scrubber composition (the first basic embodiment) or at least two different types of scrubber compositions (the second basic embodiment) which brominations remove the bromine away from the HBr which largely remains unchanged except possibly for small incidental losses, side reactions, or the like. These two types of systems and methods of operation will now be discussed separately.
Brominatable Alkylaromatic Scrubber Systems and Methods of Operation As noted above, the first basic embodiment of this invention is a process for purification of gaseous anhydrous HBr contaminated with elemental bromine, which process comprises feeding the bromine-contaminated gaseous anhydrous HBr into countercurrent contact with at least one liquid alkylaromatic hydrocarbon within a packed section of a column while maintaining such packed section under free radical bromination conditions so that one or more than one liquid α-bromoalkylaromatic compound is produced along with one mole of gaseous HBr. Typically the reaction occurs within a heated column such that the reaction zone temperature is less than about 80° C. and the average contact time within the column is less than about 12 seconds. However, in some embodiments of the invention the reaction zone temperature is in the range of about 80 to about 105° C., and, in others, preferably in the range of about 85 to about 101° C. In conducting this process it is desirable to separately recover (i) gaseous HBr from which at least 98% of the free bromine has been removed and (ii) the one or more than one liquid α-bromoalkylaromatic hydrocarbon. This separation makes it possible to feed at least a portion of the recovered gaseous HBr of (i) into contact with one or more subsequent liquid phases at least one of which contains an aromatic ether and a Lewis Acid bromination catalyst to remove small amounts of residual bromine that may be present therein. Such contact is typically conducted within a heated column such that the reaction zone temperature is greater than about 80° C., e.g., in the range of about 80 to about 101° C. and the reaction time within the column is less than about 12 seconds. The processes referred to in this paragraph are preferably conducted on a continuous or semi-continuous basis as this enables large quantities of continuously-produced bromine-contaminated gaseous anhydrous HBr to be purified on an economical basis.

It is to be understood that when using a brominatable alkylaromatic scrubber embodiment of this invention the scrubber can include only one species or a plurality of different species as long as the different individual species all are within the category of the brominatable alkylaromatic scrubber. To illustrate the brominatable alkylaromatic scrubber can be a quantity of a single liquid alkylaromatic hydrocarbon, e.g., ethylbenzene or n-butylbenzene, etc. or (ii) a liquid mixture of different alkylaromatic hydrocarbons that are brominatable on the α-carbon atoms of at least a substantial portion of the alkyl groups, e.g., a liquid mixture of $C_1$-$C_8$ alkylbenzenes. Likewise the corresponding α-bromoalkylaromatic derivatives can be present as a part of the brominatable alkylaromatic scrubber. Also, when using a brominatable alkylaromatic scrubber embodiment, there can be one or more than one scrubbing unit capable of utilizing countercurrent flows, such as a packed column at least equipped with incoming feed lines at or near the top and at or near the bottom of the column plus appropriate associated pumping means. All that is required when more than one scrubbing unit is used is that separate portions of the same type of scrubber composition (i.e., a liquid composition comprising an alkylaromatic hydrocarbon that is brominatable on the α-carbon atom of an alkyl substituent). However these same types of scrubber composition can differ from each other. For example one scrubber unit may contain octylbenzene and optionally some α-bromooctylbenzene whereas another scrubber unit may contain a liquid mixture of $C_6$-$C_{10}$ monoalkylbenzenes and optionally some α-bromo $C_6$-$C_{10}$ monoalkylbenzenes, these two compositions falling within the category comprising liquid alkylaromatic hydrocarbons that are brominatable at least in part on the α-carbon atom of an alkyl substituent on an aromatic ring. Preferably the alkyl substituent groups of such individual or mixtures of compounds contain a substantial portion (at least 15 wt % of liquid alkylaromatic hydrocarbons in which the alkyl groups contain two or more carbon atoms each.

A few additional non-limiting examples of alkylaromatic hydrocarbons that are brominatable on a α-carbon atom of an alkyl substituent on the aromatic ring(s) under the conditions utilized in the practice of this invention include n-pentylbenzene, α-methylnaphthalene, xylene, 1-ethyl-3-isopropylbenzene, 4-methylbiphenyl, liquid styrene oligomers and liquid p-methylstyrene oligomers. Liquid mixtures of two or more of the foregoing can be used. Liquid styrenic brominatable alkylaromatic scrubbers have been found especially effective (e.g., note Example 7 hereinafter). It is to be noted that when practicing the brominatable alkylaromatic scrubber embodiment of this invention, the brominatable alkylaromatic hydrocarbon(s) should be in the liquid state of aggregation at least at the temperature(s) being utilized in the packed column(s). Thus even though the brominatable alkylaromatic hydrocarbon(s) are solid at room temperature they may be used as the scrubber provided that they are in the liquid state (preferably in a flowable liquid state) at the temperatures prevailing within the packed column(s).
Multiple Scrubber-Type Systems and Methods of Operation The multiple scrubber-type systems such as a dual scrubber type system used pursuant to the second basic embodiment of this invention will of course utilize at least two different types of scrubber compositions in separate scrubber units. From the simplicity standpoint a dual system using two different types of liquid scrubbing compositions as described herein is economically desirable. However, if desired there can be more than two scrubber units using two or more than two different types of liquid scrubbing compositions as described herein.

The single and the multiple scrubber-type systems and methods of operation described above can also include a unit containing activated carbon or the like in order to remove volatile organic impurities which may be present in the initial gaseous anhydrous HBr/$Br_2$ stream.

Thus the two different scrubber compositions (or more such scrubber compositions, if desired) used in this invention are brominatable materials, i.e., the respective scrubber compositions whether unbrominated or partially brominated or a combination of these, are able to be brominated or further brominated under the conditions specified herein. All that is required is that at least a substantial amount (e.g., 10-30%) of the first or second aromatic scrubbing liquid that is present as a scrubbing liquid is able to be brominated. Preferably, the primary and secondary scrubber compositions are not brominated beyond the point of having an average number of two bromine atoms substituted on the molecules of the respective scrubber compositions (i.e., they have a bromine number no greater than about 2).

The primary scrubber composition referred to in A) above is comprised of:
(1) a mixture comprising about 5 to about 30 wt % of 1,2-diphenylethane and in the range of about 80 to about 95 wt % of a mixture containing 1,4'-bis(phenethyl) benzene and 1,4'-bis(phenethyl)bibenzyl, or
(2) a partially brominated composition of (1), and
(3) a mixture of (1) and (2).

A preferred source of the mixture of (1) is from a plant operation in which high purity 1,2-diphenylethane (DPE) is produced. Such operation typically has available a stream of crude 1,2-diphenyl ethane, which contains small amounts of benzene and other impurities (commonly referred to as "crude DPE" and a supply of product column bottoms commonly referred to as "DPE/heavies" or "DPE/h". Analysis of such column bottoms by GC-MS has revealed that these bottoms are composed of approximately an equal mixture of a three- and a four ring product apparently formed. The following equations depict the idealized reactions involved in forming DPE, and the three-ring and four-ring products of DPE/h.

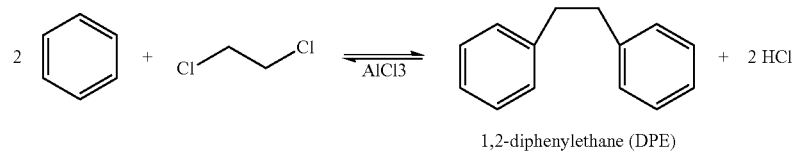

1,2-diphenylethane (DPE)

The initial product of the reaction, DPE, is considerably more reactive than benzene such that the yield becomes limited to ca. 75-78% depending upon the amount of excess benzene used. Thus "crude DPE" includes some of the unreacted benzene as well as small amounts of other reaction product impurities. The following equations depict the reactions by which the three-ring and four-ring higher oligomers of DPE are apparently produced.

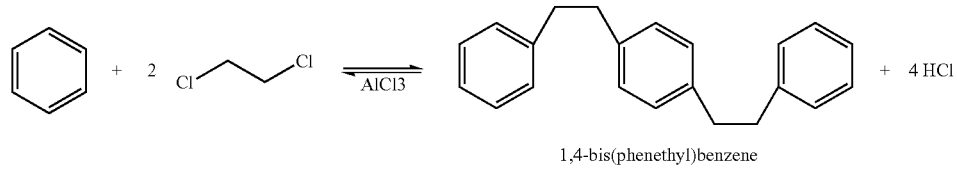

1,4-bis(phenethyl)benzene

A portion of the 1,4-bis(phenethyl)benzene (a three-ring product, not depicted below) apparently reacts with benzene to form a four-ring product as follows:

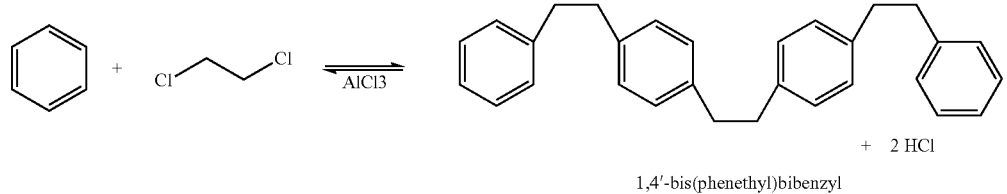

1,4'-bis(phenethyl)bibenzyl

Some of the 1,4-bis(phenethyl)benzene also undergoes a Friedel-Crafts reaction with 1,2-dichloroethane to form additional 1,4'-bis(phenethyl)bibenzyl as follows:

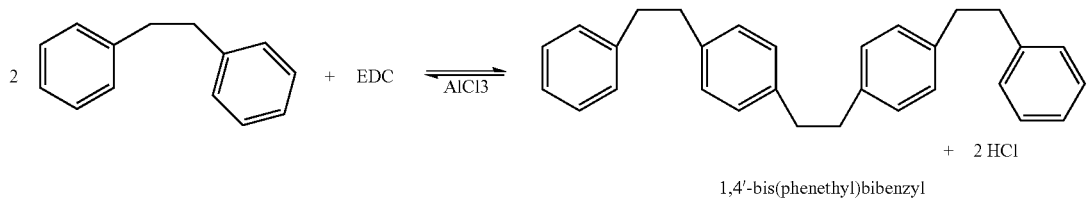

1,4'-bis(phenethyl)bibenzyl

Higher oligomers occur to a significantly lesser extent. While in theory the reactions are reversible, especially with higher loadings of $AlCl_3$, removal of HCl gas shifts the equilibrium to the right, as indicated above. Other sources of impurities can arise from use of impure benzene, from purification of DPE, and from other sources such as oxidized DPE. These compounds, which include the three- and four-ring components above and up to 10 weight percent DPE, comprise the mixture described as "C44 bottoms" in the Examples below.

The scrubber reaction vessels used in the practice of this invention can be the same or different from each other. Also, various types of scrubber vessels can be used depending upon a number of factors. Such factors include, among others, the volume and rate of production of gaseous anhydrous HBr and bromine to be processed, the rate at which such gaseous mixtures are to be treated, the type of process equipment already available on the premises that can be utilized in the process, the total costs of constructing and operating the facility, the efficiency of operation needed or desired, and so on.

Among reaction vessels, where applicable, that can be selected for use in plant facilities include, for example, (i) stirred pot reactors suitably equipped with controllable gas inlet and outlet lines, controllable heating equipment and various other necessary auxiliaries such as pumps and the like: (ii) packed columns suitably equipped, for example, with temperature controlled sumps, gas inlet and outlet lines and gas recirculation lines, controllably heating equipment and if needed or desired, and preferably having the packed columns jacketed or thermally insulated. There are various ways to achieve the conditions described. For instance, one could merely use a jacketed vessel, such as conventional reaction flask or a jacketed gas absorber bottle, in which a gas was introduced subsurface into a body of the liquid. Alternatively, a jacketed column or a packed column within a steam-heated or electrically-heated tubular furnace can accomplish similar thermal profiles. In the latter (furnace) instance, a preferred material of construction would most probably be quartz. For short contact or average residence time processing (e.g., ten seconds or less) of large volumes of continuously produced gaseous mixtures of HBr and bromine to be fed into the first packed column at a rate of 0.032 cubic feet per minute, use of two or more packed columns are generally preferred.

Generally speaking, the temperatures in the primary scrubbing operations are in the range of about 85 to about 101° C. The secondary scrubbing operations are typically conducted at temperatures in the range of about 48 to about 60° C. However departures from both or either of these ranges are permissible whenever deemed necessary or desirable. To effect the heating of the scrubbing compositions various methods can be employed including use of electrical heaters equipped with good temperature control systems, use of jacketed lines or vessels containing a flow of hot heat transfer fluid, use of steam tracing, or other suitable methods.

The processes of this invention can be conducted in a batch, semi-batch, or continuous mode of operation. Continuous operation is preferred, especially in plant operations wherein a continuous supply of gaseous anhydrous HBr and bromine is available. When operating in a continuous mode it is important to continuously or periodically replenish the primary and secondary scrubber compositions such as by providing a circulating inventory of each scrubber composition with controlled continuous or periodic feeding of fresh scrubber compositions and with controlled continuous or removal of used scrubber compositions.

Irrespective of whether the plant operation is to be conducted on a batch, semi-batch, or continuous basis, the initial feed of primary scrubber composition to the first scrubber reaction vessel at startup of operation can be a fresh unbrominated mixture comprising alkylated aromatics to include, but not limited to, DPE monomer and oligomers thereof, such as 1,4'-bis(phenethyl)benzene and 1,4'-bis(phenethyl) bibenzyl. The ranges of composition can include up to 30% DPE monomer or a brominatable partially brominated substrate composition previously formed in a prior scrubbing operation of this invention or a combination of a fresh unbrominated mixture and a brominatable partially brominated composition. See also the description given in subparagraph A) parts (1), (2), (3), which description appears hereinabove in the section under the heading "BRIEF NON-LIMITING SUMMARY OF THE INVENTION". As also noted hereinabove it is preferred that no bromination catalyst be used with such primary scrubber compositions, although aluminum chloride and/or aluminum bromide may be used as catalyst with such primary scrubber compositions, if desired.

A schematic process flow diagram illustrating desirable ways of carrying out a process of this invention is depicted in FIG. 1. As shown therein, the system depicts a preferred embodiment in which pursuant to the second basic embodiment, at least two different scrubber compositions are utilized in two separate but operatively connected scrubbing units. Thus, the system as depicted is comprised of a first reaction vessel (a first scrubbing unit) which in the form depicted is a column 10 containing a bed of packing 12, and a second reaction vessel (a second scrubbing unit) which in the form depicted is a column 20 containing a bed of packing 22. Packed columns 10 and 20 are each provided with a recirculation line (sometimes referred to as a pump-around loop) 15 and 25 respectively. Pump 16 propels the liquid contents in line 15 upwardly and into the upper free space portion 13 of column 10, or alternatively (and not as shown), directly into the upper portion of packing 12. Similarly pump 26 propels the contents of line 25 upwardly and into feed line 24 which introduces both fresh and used scrubber composition into the upper free space portion 23 of column 20, or alternatively (and not as shown), directly into the upper portion of packing 22. Feed line 14 provides fresh primary scrubber composition into the upper free space portion 13 of column 10, or alternatively (and not as shown), directly into the upper portion of packing 12. Feed line 17 provides a flow of the gaseous anhydrous HBr and bromine into the lower free space portion 11 of column 10, or alternatively (and not as shown) directly into the lower portion of packing 12. Line 18 transports partially debrominated gaseous HBr from the upper portion of column 10 into the lower portion of column 20. This gaseous flow can be propelled by an additional blower (not shown) inserted in line 18. Line 19 receives used scrubber composition from the lower portion 11 of column 10 and transports this liquid flow either upwardly through recirculation line 15 for recycle through column 10 or via discharge line 45 to quenching vessel 40 in which catalyst residue is suitably deactivated before discharge via line 42 to a unit which recovers the bromine values that have been removed from the gaseous stream of HBr and bromine processed in the separation system of the invention (not shown), thereby enabling the separation and separate recovery of both HBr and free bromine from the original gaseous mixture of these components. Line 44 provides a suitable liquid phase catalyst deactivating composition into quenching vessel 40 as needed. Line 29 receives used scrubber composition from the lower portion 21 of column 20 and transports this liquid flow either upwardly through recirculation line 25 for recycle through column 20 or via quench line 45 to quenching vessel 40 for deactivation of catalyst residue as previously described above. Line 28 receives purified gaseous HBr from the upper portion 23 of column 20 and transports it through purification vessel 30 for removal of gaseous or entrained organic impurities that may be present in the purified gaseous HBr stream. A pump (not shown) may be inserted in line 28 to facilitate the flow of purified gaseous HBr from column 20 through purification vessel 30 for storage or use in other plant facilities.

As seen from the above, the flows into the upper portions of columns 10 and 12 and into the bottom portions of columns 10 and 12 are countercurrent flows. It will also be seen that fresh supplies of primary scrubber composition either alone or together with a recycled supply of primary scrubber composition can be fed into the upper free space 13 of column 10 or directly into the upper portion of packing 12 in column 10. Similarly, fresh supplies of secondary scrubber composition either alone or together with a recycled supply of secondary scrubber composition can be fed into the upper free space 23 of column 20 or directly into the upper portion of packing 22 in column 20. The selection of the make up for these respective feeds to their respective columns is desirably controlled by correlation of the relative amounts of feed so as to maintain a molar ratio of bromine to aromatic of less than 1.16, calculated on a 1,2-diphenylethane monomer basis. In the proposed secondary scrubber system, it has been found that density of the scrubber liquid helps provide guidance as to the bromine:aromatic molar ratio.

It is to be noted that in the system as depicted and described above the scrubbing compositions fed into columns 10 and 20 via lines 14 and 24, respectively, are of two different types, one being a primary scrubber composition as described herein which removes a substantial amount (i.e., greater than 90%,) of the bromine from the initial gaseous mixture of HBr contaminated with bromine. The other type of scrubber used in column 20 is a secondary scrubber composition, as described herein, which removes residual bromine from the gaseous stream entering the secondary scrubber. The scrubber composition in column 20 is of a different type and has a different composition from that used in column 10.

FIG. 1 can also depict the first basic embodiment of this invention in which only one type of liquid scrubbing composition is used (i.e., pursuant to the brominatable alkylaromatic scrubber embodiment of this invention). One way of accomplishing this is to simply replace line 18 by line 28 and purification vessel 30, and eliminate from FIG. 1 all of the elements depicted by a numeral in the range of 20 to 29. Another way of utilizing only one type of liquid scrubbing composition in the system is to use the system as depicted in FIG. 1 and to simply feed via feed lines 14 and 24 separate portions of the same type of liquid scrubber composition used pursuant to this invention in the embodiments in which only one type of scrubber composition is used and described herein.

In the following Examples laboratory scale equipment was used to establish the capability and effectiveness of a process and system of this invention when conducted on an industrial scale. The process allows for purification of HBr in the context of limited supply of currently used diphenyl oxide as a scrubbing material. The scrubber processes and systems of this invention protect critical equipment including an anhydrous HBr compressor system from corrosion due to contact with bromine.

The laboratory scale apparatus used in Examples 1-5 was constructed to simulate individually either the primary HBr scrubber or the secondary HBr scrubber so as to model the expected gas-liquid contacting occurring in an industrial scale scrubber system of this invention. The laboratory scale apparatus included a jacketed 1-inch by 12-inch column packed with a ¼-inch ceramic saddles, 11 inches of the column providing active contacting. Recycle lines from the sump into the top of the column were traced with live steam so that the temperature of the gas-liquid contacting mixture in the primary scrubber is kept in the range of about 90 to about 95° C. A poly(tetrafluoroethylene) (PTFE) tube was inserted to insure that the gas phase delivery point would be constant at 1" from the bottoms of the packing. Temperature indicators were present in the sump and the bath used to control the column jacket. Electrical heating of the reactor/sump (a 500 mL three necked round bottomed flask) was provided by use of a 0.5 L heating mantle coupled to a Variac® transformer. In Examples 6 and 7 a similar purification system was used except that the column was an 18-inch column containing similar packing material and auxiliaries.

Example 1 serves as both a control experiment (as a check on the apparatus) and as an example of the secondary scrubber effectiveness in this context.

EXAMPLE 1

Control Experiment (DPO) Diphenyl oxide 63.72 g (0.374 mol) was added along with 1.02 g $AlCl_3$ catalyst into the three-necked 500 mL round-bottomed flask portion of the apparatus described above. These were pre-heated to 46 C and pre-circulated, via peristaltic pump, at 30 mL/min through steam-jacketed ⅛" PTFE tubing into the packed column bed described above. Bromine (90.20 g, 0.564 mol) was added into the vapor feed of $N_2$ with total gas flow of 900 mL/min. (The flow rates were chosen so as to closely match an existing plant scrubber column.) A light yellow tint in the aqueous scrubber was noted over the course of the experiment with its final color, after four hours being a yellow-gold color. The aqueous scrubber (269.25 g) was analyzed by titration for bromine then a sample was neutralized with 0.2 mL 65% hydrazine and its HBr was determined by titration with $AgNO_3$ after correction for the bromine content. It had 15.93% wt (42.89 g) HBr and 0.31 g bromine. This indicated that the HBr content in the scrubber was 93.94% of theory with a bromine breakthrough of only 0.31 g (3437 ppm of fed). Based upon the bromine fed, it produced $Br_{1.51}$ DPO.

Examples 2 through 5 illustrate some of the important features employed pursuant to this invention.

EXAMPLE 2

The procedure of Example 1 was used except the substrate was a mixture of crude DPE in DPE heavies. Thus, 67.22 g bromine (molar ratio 1.3:1.0 or $Br_2$:DPE) was fed into a pre-heated, pre-circulated mixture of 63.02 g DPE/h containing 8.47% crude DPE and 1.92 g $AlCl_3$ catalyst. At a jacket temperature of 77 C (reactor temperature 58-60 C), the starting materials were fluid and a viscosity increase was noted as the bromination progressed. After three hours of feed, flow between the reactor and the pump was inhibited so as to limit contacting, probably due to the lower reactor temperature. After analysis, the scrubber (289.41 g) contained HBr 28.39 g (83.42% of theory) with 2.81 g bromine evolved (4.18% of fed).

EXAMPLE 3

Using the procedure of Example 1, a mixture of 75% heavies were used as substrate at a jacket temperature of 72 C. Bromine (67.19 g 0.42 mol) was fed to a pre-heated, pre-circulated mixture of 42.64 g DPE/h containing 12.96 g crude DPE with 0.83 g $FeCl_3$. The jacket temperature was 72 C and the reactor sump temperature ranged generally 75-90 C. The scrubber color began as colorless and became yellow in 15 min, then yellow gold and eventually orange after 1.5 hours and orange-red after ca. 4 hours. The scrubber weight was 330.28 g and it was analyzed as described above (Example 1). It contained 27.78 g HBr (81.67% of theory) and 2.56 g of evolved bromine (3.82% of fed). The organic product was isolated and analyzed by GC which showed DPE 14.66%, Br1DPE 65.45%, Br2DPE 19.89%. The average bromine number was 1.08. TGA (10 C/min, N2 atm) showed 1% wt loss at 121.1 C, 5% at 157.4 C, and 10% at 178.6 C. DSC ($N_2$ atm) showed a minor transition at 178 C.

Examples 4 and 5 demonstrate the ability of using free radical bromination in the primary scrubber compositions employed pursuant to this invention in which no added catalyst is present.

EXAMPLE 4

No Added Catalyst

Using the procedure of Example 1 (except for use of a PTFE ⅛ inch feed line for gas input), a mixture of 20.87% DPE in heavies were used as substrate at a jacket temperature of 90° C. Bromine (70.57 g 0.44 mol) was fed to a pre-heated, pre-circulated mixture of 66.81 g DPE/h containing 17.08 g crude DPE with no catalyst added. The liquid recycle rate was 50 mL/min and it was jacketed with live steam (4 psig). The gas inlet rate was 900 mL/min. The jacket temperature was 90° C. and the reactor sump temperature ranged generally 87.7-92.0° C. The scrubber color began as colorless and became yellow in 15 min, then yellow gold and eventually orange after two hours. The scrubbers were analyzed as described in Example 1. These contained 33.60 g HBr (94.04% of theory) and 1.65 g of evolved bromine (2.34% wt of fed) for a bromine scrubbing efficiency of 97.66%.

EXAMPLE 5

No Added Catalyst and Effect of Longer Reaction Time

Using the procedure of Example 4, a mixture of 18.82% DPE in heavies were used as substrate at a jacket temperature of 90° C. Bromine (74.93 g 0.47 mol) was fed to a pre-heated, pre-circulated mixture of 71.05 g DPE/h containing 16.72 g crude DPE with no catalyst added. The liquid recycle rate was 30 mL/min and it was jacketed with live steam (4 psig). The gas inlet rate was 400 mL/min. The jacket temperature was 90° C. and the reactor sump temperature ranged generally 86.0-92.2° C., increased to ca.106° C. upon completion. The scrubber color began as colorless and became yellow after four hours and gold after eight hours, never reaching the orange coloration. The scrubbers were analyzed as described in Example 1. These contained 35.67 g HBr (94.04% of theory) and 0.246 g of evolved bromine (0.33% wt of fed) for a bromine scrubbing efficiency of 99.67%.

Example 6 illustrates a preferred embodiment of this invention wherein elevated temperatures and relatively low flow rates are used in order to achieve extremely high amounts of bromine removal using only a single especially preferred scrubber of this invention which comprises plant bottoms containing 1,2-diphenylethane, and oligomers thereof, such as 1,4'-bis(phenethyl)benzene and 1,4'-bis(phenethyl)bibenzyl and no bromination catalyst. In other words the bromination was conducted under free radical conditions.

EXAMPLE 6

No Added Catalyst and use of High Temperatures with a Relatively Low Gas Inlet Rate Using the procedure of Example 4 in an 18-inch packed column with a ⅛" PTFE gas feed line, a 63.48 g sample of 8.76% DPE in heavies were used as substrate at a jacket temperature of 97-101° C. Bromine (64.80 g 0.405 mols) was fed to a pre-heated, pre-circulated mixture of 63.48 g heavies (8.76% DPE, GC area percent) with no catalyst added. The liquid recycle rate was 50 mL/min and it was jacketed with live steam (3 psig). The gas inlet rate was 400 mL/min. The jacket temperature was 97-100° C. and the reactor sump temperature ranged generally 96-107° C., increased to ca.107° C. upon completion. The scrubber color began as colorless and became yellow after two hours and gold after five hours, never reaching the orange coloration. The scrubbers were analyzed as described in Example 1. These contained 30.06 g HBr (91.62% of theory) and 0.25 g of evolved bromine (0.39% wt of fed) for a bromine scrubbing efficiency of 99.61%.

EXAMPLE 7

The procedure of Example 6 was repeated except as noted. A mixture of styrenic oligomers (average ring number=2.1) was used as the scrubber at a jacket temperature of 92-94° C. Bromine (69.52 g 0.435 mol) was fed to a pre-heated, pre-circulated mixture of 65.36 g of styrene oligomers and no catalyst was added. The liquid recycle rate was 50 mL/min and, unlike Example 6, the recycle liquid line was not jacketed with live steam. The gas inlet rate was 400 mL/min. The reactor sump temperature ranged generally from 63 to 68° C. The scrubber color began as colorless and became yellow after three hours yet never reaching the orange coloration after six hours total feeding time. The HBr absorber was analyzed as described in Example 1. It contained 34.66 g HBr (98.49% of theory) and 0.15 g of evolved bromine (0.22% wt of fed) for a bromine scrubbing efficiency of 99.78%. The organic product was isolated as a gold liquid.

As used in the ensuing claims "contact time" means the time that the gaseous mixture and the liquid scrubber composition are in reactive contact with each other within a packed bed or other structure facilitating intimate mutual contact on a surface having a high surface area (e.g., a total surface area of at least 0.3 $in^2$ per 0.14 g packing in the above-described column).

Fluidity Improvement for Purification of Anhydrous HBr Containing Bromine

Diphenyl oxide (DPO) has been used successfully as a scrubbing medium for this purification step for over 20 years. The Br1,4DPO contains trace $AlCl_3$ which insures dryness during its conversion into decabromodiphenyl oxide (DBDPO). With the recent environmental initiatives, commercial production of DBDPO is being replaced by production of decabromodiphenylethane (DBDPE). The production process for DBDPE makes available both diphenylethane (DPE) as a raw material and a heavy ends liquid product sometimes referred to as DPE/h. McKinnie (U.S. Pat. No. 7,408,088) examined the analogous scrubbing process using DPE with $FeCl_3$ catalyst and noted the difficulty of iron catalyst removal and traces of unavoidable side chain bromination.

Our initial tests showed that the kinetics of ring bromination using $AlCl_3$ was too slow relative to DPO. We observed that DPE has limited capacity for bromine scrubbing, limited mainly by the kinetics and viscosity effects. A breakthrough came when we noted the rapid side chain bromination that occurred at 88-92° C. This allows for an equimolar reaction between bromine and DPE to occur within a few seconds—the timescale necessary to allow use of a heated column scrubber. Further testing of the dehydrobromination rates and viscosities appear promising, as described in the results section below. Dual scrubber use, such that DPE/h is used in the primary scrubber and DPO is used as a polishing scrubber, has been explored.

The present improvement involves in part the discovery that a fluidizer is needed for a wider, more robust temperature range for efficient scrubbing operations using DPE/h as a scrubber. Further, pursuant to this embodiment of the invention, it has now been found that tetrahydronaphthalene (THN) is well-suited for use as an efficient and highly effective fluidizer for this purpose.

Free radical bromination of molten 1,2-diphenylethane and its oligomers (DPE/h) occurs by generation of the reactive site, a secondary benzyl radical on the side chain. Here the reaction with bromine occurs and is especially facile at 88° C., allowing the bromination to occur within the kinetic limitations of a few seconds reaction time. This generates 1-bromo-1-2-diphenylethane for DPE monomer and the analogous side chain products for the oligomers. One mole of HBr is generated per mole of bromine reacted. An example of the side chain reaction for the three-ring component is illustrated below:

Apparatus used for Vapor Phase Brominations of DPE/h Mixtures

A jacketed 1"×18" column packed with ¼" ceramic saddles (16" active contacting) was constructed to simulate the HBr scrubber so as to model the expected gas-liquid contacting. Recycle lines from the sump into the top of the column were traced with live steam. A ⅛" PTFE tube was inserted to insure that the gas phase delivery point would be constant at 2" from the bottoms of the packing. Temperature indicators were present in the sump and the bath used to control the column jacket. Electrical heating of the reactor/sump (a 500 mL three necked round bottomed flask) was provided by use of a 0.5 L heating mantle coupled to a Variac.

EXAMPLE 8

High Gas Flow, High Temperature

Samples of C41 bottoms and C44 bottoms (heavies) were preheated to 62° C. to melt it over 12 hours. These were mixed as C41 bottoms (17.41 g) with C44 bottoms (46.73 g) during addition into a preheated 500 mL round bottomed flask. It and the apparatus, including reactor sump and all line tracing was brought to the target temperature of 95° C. for Br1.10 DPE/h. Molten DPE/h was circulated through heat-traced lines through the column scrubber for 12-15 minutes prior to introducing bromine vapor. This was to pre-wet the packed column. Bromine 62.36 g (0.39 mol) was added as vapor via nitrogen carrier gas at the non-optimal rate of 900 mL/min through a ⅛" PTFE line through the internal of the column to approximately 2" from the column bottoms where it was released for countercurrent contacting with the liquid DPE/h. The liquid recycle rate was 50 mL/min with 3 psig steam tracing of the ⅛" recycle line. Near the end of this experiment, it was noted that the fluidity of the reaction mixture was decreasing.

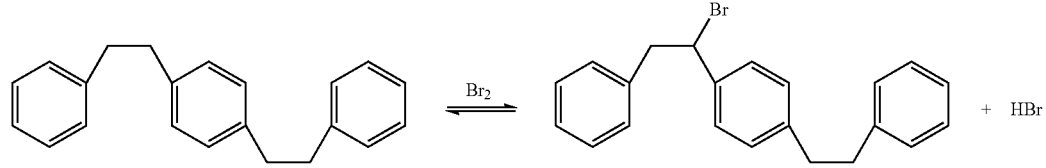

By design the primary column scrubber uses free radical bromination, which is sufficiently fast at 88° C. This temperature provides for a fluid, reactive scrubber only for up to Br0.8DPE/h. Higher extent of bromination, such as to Br1.2DPE!h, yields a higher viscosity organic phase which requires higher temperatures (92-95 C) for flowability. Under these circumstances it is essential to limit the time at temperature by prompt turnover of the primary scrubber and replenishment with fresh DPE/h. If this is not performed after the designed feed of Br1.2DPE/h then the organics can become immobile (freeze up) due to either overbromination (a viscosity effect) or from dehydrobromination and subsequent degradation of the initial olefin.

TABLE 1

Column Scrubber Bromination of 80/20 wt
C44 Bottoms/DPE at 95° C., 900 mL/min Gas

| Elapsed Time (min) | Col Jacket Temp. (° C.) | Rx Sump Temp (° C.) | Color of HBr absorber | Good Liq Flow? Y/N |
|---|---|---|---|---|
| 0 | 95 | 89.3 | colorless | Y |
| 2 | 95 | 89.9 | Yellow | Y |
| 14 | 95 | 90.4 | Gold | Y |
| 22 | 94 | 89.6 | orange | Y |
| 41 | 94 | 90.0 | orange | Y |
| 75 | 94 | 88.4 | orange | Y |
| 95 | 92 | 89.9 | orange | Y |

TABLE 1-continued

Column Scrubber Bromination of 80/20 wt
C44 Bottoms/DPE at 95° C., 900 mL/min Gas

| Elapsed Time (min) | Col Jacket Temp. (° C.) | Rx Sump Temp (° C.) | Color of HBr absorber | Good Liq Flow? Y/N |
|---|---|---|---|---|
| 107 | 93 | 89.6 | orange | Y |
| 117 | 92 (refilled) | 89.0 | orange | Y |
| 137 | 93 | 89.9 | orange | Y |
| 152 | 94 | 90.2 | orange, absorber 2 | Y |
| 167 | 94 | 90.4 | yellow | Y |
| 187 | 93 | 90.2 | gold-orange | Y |
| 195 | 88 (refilled) | 90 | gold | Y |
| 209 | 90 | 91.3 | gold | Y |

EXAMPLE 9

Low Gas Flow, High Temperature

Effect of Lower Gas Flow Rate

The procedure of Example 8 was used except as noted below. Preheated C41 bottoms (16.08 g) was combined with C44 bottoms (49.24 g) during addition into a preheated 500 mL round bottomed flask. The column reactor was held at generally 94-96° C. and the reactor sump was preheated to 85-90° C. and was slowly heated, holding generally at 94-96° C. over most of the experiment. Molten DPE/h was circulated through heat-traced lines through the column scrubber for 12-15 minutes prior to introducing bromine vapor. This was to pre-wet the packed column. Bromine 69.18 g (0.432 mol) was added as vapor via nitrogen carrier gas at 400 mL/min. The liquid recycle rate was 50 mL/min with 3 psig steam tracing of the ⅛" recycle line. We isolated 54.87 g by pumping through steam traced ⅛" PTFE line. The HBr absorbed was 30.51 g (87.12% of theory), and the bromine in the absorber was 0.04 g (0.06% of fed). Near the end of this experiment, it was noted that the fluidity of the reaction mixture was decreasing.

TABLE 2

Column Scrubber Bromination (to Br 1.21 DPE/h) at
95° C., 400 mL/min Gas

| Elapsed Time | Col Jacket Temp (° C.) | Rx Sump Temp (° C.) | Color of HBr absorber | Good Liq Flow? Y/N |
|---|---|---|---|---|
| 0 | 94 | 84.5 | Colorless | Y |
| 12 | 94 | 88.4 | Colorless | Y |
| 27 | 94 | 89.8 | Colorless | Y |
| 42 | 95 | 89.3 | Colorless | Y |
| 57 | 95 | 91.9 | Colorless | Y |
| 72 | 92 | 90.7 | Colorless | Y |
| 102 | 97 | 94.0 | Colorless | Y |
| 142 | 95 | 93.8 | Colorless | Y |
| 157 | 96 | 94.4 | Colorless | Y |
| 192 | 95 | 95.9 | Colorless | Y |
| 222 | 95 | 95.6 | Lt yellow | Y |
| 249 | 93 | 96.0 | Lt yellow | Y visc inc |
| 284 | 95 | 97.1 | Lt yellow | Y |
| 296 | 93 | 94.7 | Lt yellow | Y visc inc |
| 309 | 94 | 96.4 | Lt yellow | Y |
| 382 | 94 | 95.1 | Yellow | Y |

Further improvements in reaction mixture fluidity were achieved subsequent to the earlier experiments of Examples 8 and 9. These preferred improvements are illustrated in the following Examples 10-18.

EXAMPLE 10

Low Gas Flow, Lower Temperature

Free Radical Bromination of THN-C44 Bottoms Mixtures

Preheated C44 bottoms (47.57 g, 0.261 mol) was pre-mixed with THN (11.86 g, 0.090 mol) and was added into a preheated 500 mL round bottomed flask. The column reactor was held at generally 88° C. and the reactor sump was preheated to 64° C. and then slowly heated, holding generally at 63-65° C. over most of the experiment. The organics were pre-circulated through heat-traced lines through the column scrubber for 12-15 minutes prior to introducing bromine vapor. Bromine 70.67 g (0.442 mol) was added as vapor via nitrogen carrier gas at 400 mL/min. The bromine charge was selected as being the sum of (1.2×mols DPE)+1.5×mols THN). The organic liquid recycle rate was 50 mL/min with 2 psig steam tracing of the ⅛" recycle line. We isolated 49.55 g by pumping through steam traced ⅛" PTFE line. The HBr absorbed was 39.19 g (109.53% of theory), and the bromine in the absorber was 0.38 g (0.54% of fed).

TABLE 3

Column Scrubber Bromination of THN-C44
Bottoms 85° C., 400 mL/min Gas

| Elapsed Time (min) | Col Jacket Temp (° C.) | Rx Sump Temp (° C.) | Color of HBr absorber | Good Liq Flow? Y/N |
|---|---|---|---|---|
| 0 | 87.5 | 64.3 | colorless | Y |
| 15 | 87 | 63.3 | colorless | Y |
| 29 | 88 | 65.1 | colorless | Y |
| 60 | 88 | 65.1 | colorless | Y |
| 90 | 88 | 65.3 | colorless | Y |
| 120 | 88 | 66.0 | colorless | Y |
| ISO | 88 | 66.0 | colorless | Y |
| 175 | 88 | 65.6 | colorless | Y |
| 211 | 88 | 63.1 | yellow | Y |
| 240 | 88 | 64.8 | yellow | Y (a) |
| 265 | 88 | 64.8 | gold | Y (a) |
| 310 | 88 | 59.7 | gold-orange | Y (a) |
| 323 | 88 | 58.7 | gold-orange | Y (a) |

(a) turbidity observed in HBr absorber.

An additional set of experiments were carried out as above except as indicated below to illustrate preferred embodiments of this invention, using mixtures of tetrahydronaphthalene (THN) and DPE C44 bottoms as the scrubbing fluid with the gas flow rate held constant at 400 mL/min. A key measure of fluidity is the amount of organic brominated product isolated at temperature by pumping through a ⅛" PTFE line using a peristaltic pump. The amount of this isolated organic indicates that the liquid is fluid at the temperature employed. Only those with high THN content are liquid at 25° C. If the weight of organic pumped is very high (as in Examples 12 and 15) then especially preferred conditions with not only good fluidity but no significant fouling in the column or sump are achieved.

In terms of dehydrobromination (DHB) and bromine scrubbing efficiency, the results indicate that increasing the THN content to 80 wt % and the temperature (to 88° C.) increases the amount of DHB to ca. 120% of theory. Only the experiments with 20 wt % THN at 65° C. did not have higher than theoretical HBr.

TABLE 4

Column Brominations Using THN- C44/h as Solvent-Reagent

| Ex | Temp (° C.) | THN Wt % | Mass Ratio $Br_2$; Organic | Time, min to Orange | $Br_2$ wt % Reacted | HBr wt % of Theory | Organic Fluidity (a) |
|---|---|---|---|---|---|---|---|
| 11 | 87-89 | 80 | 1.29 | (b) | >99.90 | 112.18 | + |
| 12 | 65-66 | 80 | 1.08 | (b) | >99.90 | 107.80 | + |
| 13 | 64-65 | 20 | 1.24 | 85 | 91.02 | 95.76 | + |
| 14 | 65 | 20 | 1.10 | 140 | <94.18 | 95.33 | + |
| 15 | 88 | 20 | 1.08 | (b) | >99.90 | 124.16 | + |
| 16 | 87-88 | 20 | 1.30 | 23.5 | 98.30 | 122.95 | + |
| 17 | 65 | 80 | 1.27 | (b) | >99.90 | 119.36 | + |
| 18 | 87-88 | 80 | 1.08 | (b) | >99.90 | 117.40 | + |

(a) Fluidity (+) indicates isolation of organics pumped through ⅛" PTFE tubing with a peristaltic pump at 65-88° C.
(b) HBr absorber did not turn orange over the course of experiment.

As can be seen from the above description of the fluidity improvements features of this invention, this invention further includes the following embodiments:

A) A process for purification of gaseous anhydrous HBr contaminated with elemental bromine, which process comprises feeding the bromine-contaminated gaseous anhydrous HBr into countercurrent contact with at least one liquid alkylaromatic hydrocarbon within a packed section of a column while maintaining said packed section under free radical bromination conditions so that one or more than one liquid α-bromoalkylaromatic compound is produced along with one mole of gaseous anhydrous HBr wherein said at least one liquid alkylaromatic hydrocarbon comprises a mixture comprising molten 1,2-diphenylethane and its oligomers in combination with tetrahydronaphthalene in an amount that improves the fluidity of said mixture.

B) A process for purification of a gaseous mixture of anhydrous HBr containing elemental bromine, which process comprises feeding said gaseous mixture into at least one liquid scrubber composition under free radical bromination conditions so that one or more than one liquid alpha bromoalkyl(ene) aromatic compound is produced along with one mole of gaseous anhydrous HBr, wherein said alpha bromoalkyl(ene) aromatic compound comprises (i) molten 1,2-diphenylethane and at least one of its oligomers, namely, 1,4'-bis(phenethyl)benzene and 1,4'-bis(phenethyl)bibenzyl, in combination with (ii) a fluidizer amount of tetrahydronaphthalene.

C) A process as in B) wherein the weight ratio of (i):(ii) is in the range of 3.5-4.5:1.0 and preferably in the range of about 80:20.

Unless expressly stated otherwise, the term "liquid" as used herein, including the claims, means that the substance is in the liquid state at the temperature of the operation in which the substance is to be used or is being used even though the substance may be in the form of a solid at room temperature. Also the term "brominatable alkylaromatic hydrocarbons" as used herein including the claims has the same meaning as the term "brominatable alkylaromatic scrubber" as defined earlier in this document.

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

The invention may comprise, consist or consist essentially of the materials and/or procedures recited herein.

The chemical formulas given in this document are not intended to limit depicted molecules to any given spatial configurations. Rather they depict the chemical composition of the molecules.

This invention is susceptible to considerable variation in its practice. Therefore the foregoing description is not intended to limit, and should not be construed as limiting, the invention to the particular exemplifications presented hereinabove.

That which is claimed is:

1. A process for purification of gaseous anhydrous HBr contaminated with elemental bromine, which process comprises forming one or more than one liquid α-bromoalkylaromatic compound and gaseous anhydrous HBr having a reduced content of bromine by feeding the bromine-contaminated gaseous anhydrous HBr into countercurrent contact with at least one liquid alkylaromatic hydrocarbon within a packed section of a column and maintaining said packed column under free radical bromination conditions without use of added bromination catalyst and at temperature(s) within the range of 80-105° C. for an average reaction time of less than 12 seconds whereby gaseous anhydrous HBr having a reduced content of bromine and said one or more than one liquid α-bromoalkylaromatic compound and are formed.

2. The process as in claim 1 wherein the said reaction zone temperature is in the range of about 85 to about 101° C.

3. The process as in claim 1 further comprising separately recovering gaseous HBr from which at least 98% of the free bromine has been removed.

4. The process as in claim 3 further comprising feeding at least a portion of the recovered gaseous HBr into contact with one or more subsequent liquid phases at least one of which contains an aromatic ether and a Lewis Acid bromination catalyst to remove small amounts of residual bromine that may be present therein.

5. The process as in claim 1 wherein said at least one liquid alkylaromatic hydrocarbon comprises (i) 1,2-diphenylethane, 1,4'-bis(phenethyl)benzene, or 1,4'-bis(phenethyl)bibenzyl, or any liquid mixture comprising of any two or all three thereof, or (ii) a styrenic brominatable alkylaromatic scrubber.

6. The process as in claim 1 wherein said process is conducted on a continuous or semi-continuous basis.

7. The process as in claim 1 wherein said at least one liquid alkylaromatic hydrocarbon comprises a mixture comprising molten 1,2-diphenylethane and its oligomers in combination with a fluidizer amount of tetrahydronaphthalene.

8. A process of removing bromine from a gaseous mixture comprising hydrogen bromide and bromine, which process comprises:
   passing said gaseous mixture into contact with a primary scrubber composition that removes a substantial amount of the bromine from said gaseous mixture, and passing the resultant partially debrominated gaseous mixture into contact with a secondary scrubber composition that removes additional bromine from the gaseous HBr;
A) wherein said primary scrubber composition comprises:
   (1) a mixture comprising alkylated aromatics containing 1,2-diphenylethane in an amount of up to about 30 wt %, or
   (2) a brominatable partially brominated substrate composition of (1), or
   (3) a mixture of (1) and (2); and
   wherein said primary scrubber composition is free of any added bromination catalyst;
B) wherein said secondary scrubber composition comprises
   (4) an aluminum chloride and/or aluminum bromide bromination catalyst,
   (5) one or more activated aromatic compounds that
      (i) are thermally stable at 70° C. under nitrogen, and
      (ii) are chemically and thermally stable in the presence of HBr at least up to 120° C.;
   (6) a partially brominated derivative of any one or more of the components of (5); and
C) wherein said primary and secondary scrubber compositions are kept at temperature(s) that during the scrubbing operation maintain these respective scrubber compositions in flowable liquid states.

9. The process as in claim 8 wherein said gaseous mixture and said primary scrubber composition are contacted as countercurrent flows through a first reaction vessel, and wherein said resultant partially debrominated gaseous mixture and said secondary scrubber composition are contacted as countercurrent flows through a second reaction vessel.

10. The process as in claim 9 wherein at least said first reaction vessel is a packed column, or wherein said second reaction vessel is a packed column, or wherein said first reaction vessel and said second reaction vessel are both separate packed columns.

11. The process as in claim 9 wherein said first reaction vessel is a first packed column and said second reaction vessel is a second packed column, wherein said gaseous mixture is fed into said first packed column below or into the bottom portion of the packing in said first packed column and leaves said first packed column from or above the upper portion of the packing in said first packed column, and wherein said resultant partially debrominated gaseous mixture is fed into the said second packed column below or into the bottom portion of the packing in said second packed column and leaves said second packed column from or above the upper portion of the packing in said second packed column.

12. The process as in claim 8 wherein said primary scrubber composition comprises a mixture comprising alkylated aromatics includes 1,4'-bis(phenethyl)benzene and/or 1,4'-bis(phenethyl)bibenzyl.

13. The process as in claim 8 wherein said one or more activated aromatic compounds comprises 1,2-diphenylethane, 1,4-diphenoxybenzene, bisphenol-A or diphenyl ether, or mixtures of any two or more of these materials.

14. The process as in claim 8 wherein said resultant purified gaseous HBr is passed into and through a bed of carbon particles.

15. The process as in claim 11 wherein said first packed column is equipped with a feed line of fresh primary scrubber composition, a recirculation line and a pump disposed such that said primary scrubber composition enters said first packed column at the top of said first packed column and a portion of the scrubber composition continues to flow through the recirculation line and another portion of the scrubber composition is introduced into and through a non-aqueous quenching liquid to destroy residual catalyst, if any, in the primary scrubber composition passing into and through said quenching liquid, and wherein said second packed column is equipped with a feed line of a recirculation line and a pump disposed such that said secondary scrubber composition enters said second packed column at the top of said second packed column and a portion of the scrubber composition continues to flow through the recirculation line and another portion of the scrubber composition is introduced into and through a non-aqueous quenching liquid to destroy residual catalyst in the secondary scrubber composition passing into and through said quenching liquid.

16. The process as in claim 8 wherein each of said contact times is about 10 seconds or less.

17. The process as in claim 8 wherein said gaseous mixture that is passed into contact with a primary scrubber composition is fed into said primary scrubber composition at an anhydrous HBr flow rate in the range of about 300 to about 900 mL per minute.

18. The process as in claim 17 wherein said anhydrous HBr flow rate in the range of about 300 to about 400 mL per minute.

19. A process for purification of a gaseous mixture of anhydrous HBr containing elemental bromine, which process comprises feeding said gaseous mixture into at least one liquid scrubber composition comprising at least one liquid alkylaromatic hydrocarbon under free radical bromination conditions so that one or more than one liquid α-bromoalkylaromatic compound is produced along with gaseous anhydrous HBr, the liquid scrubber composition also comprising a fluidizer which is tetrahydronaphthalene.

20. The process as in claim 19 wherein said liquid alkylaromatic hydrocarbon comprises (i) molten 1,2-diphenylethane and at least one of its oligomers, namely, 1,4'-bis(phenethyl)benzene and 1,4'-bis(phenethyl)bibenzyl, and wherein the weight ratio of (i) to fluidizer (ii) is in the range of 3.5-4.5:1.0.

21. The process as in claim 20 wherein the weight ratio of (i):(ii) is in the range of about 80:20.

* * * * *